United States Patent [19]

Axen et al.

[11] 4,048,416
[45] Sept. 13, 1977

[54] THIOPOLYMERS, THEIR DERIVATIVES AND METHODS FOR THEIR PREPARATION AND USE

[75] Inventors: Rolf Erik Axel Verner Axén, Balinge; Jerker Olof Porath; Per Jan Erik Carlsson, both of Uppsala, all of Sweden

[73] Assignee: Exploaterings Aktiebolaget T.B.F., Stockholm, Sweden

[21] Appl. No.: 580,814

[22] Filed: May 27, 1975

[30] Foreign Application Priority Data

May 30, 1974 Sweden .......................... 7407173

[51] Int. Cl.² ................................. C07H 15/04
[52] U.S. Cl. .................................. 526/9; 195/63; 195/68; 210/24; 260/6; 260/112 R; 526/11; 526/30; 526/41; 536/116; 536/120; 536/122
[58] Field of Search ................. 195/63, 68; 210/24 C; 260/112 R, 6, 209, 209 D, 212, 209.6; 536/120, 116, 122

[56] References Cited
U.S. PATENT DOCUMENTS

| | | | |
|---|---|---|---|
| 3,019,171 | 1/1962 | Bloch et al. | 195/68 |
| 3,380,999 | 4/1968 | Grötsch | 536/116 |
| 3,627,683 | 12/1971 | Adam et al. | 195/68 |
| 3,651,041 | 3/1972 | Schell et al. | 536/122 |
| 3,753,861 | 8/1973 | Forgione | 195/68 |
| 3,836,433 | 9/1974 | Wirth et al. | 195/68 |
| 3,853,708 | 12/1974 | Porath et al. | 195/68 |
| 3,904,478 | 9/1975 | Dean et al. | 195/68 |
| 3,962,037 | 6/1976 | Mitchell | 195/68 |

*Primary Examiner*—Edward M. Woodberry
*Attorney, Agent, or Firm*—Young & Thompson

[57] ABSTRACT

A method for producing products for separation, ion exchange or as basic material for the preparation of various derivatives designed for separation purposes and adsorption purposes by means of a polymer being activated with a reagent containing at least two bifunctional groups so that at least one of the reactive, functional groups in each molecule is bonded to the polymer while leaving a considerable amount of remaining groups unreacted but still reactive so that the activated polymer can be caused to react with thiosulphate after surplus reagent has been eliminated. The invention also relates to the produced products or their derivatives consisting of a water-soluble hydroxyl group or amino group containing polymer substituted with organic side-chains, each containing one or more thiosulphate groups or derivatives of such groups and the use of the products for purification of water, separation, immobilization of enzymes, etc.

29 Claims, 2 Drawing Figures

THIOPOLYMERS, THEIR DERIVATIVES AND METHODS FOR THEIR PREPARATION AND USE

A great many methods based on adsorption, particularly chromatographic, are available for the separation, purification and isolation of constituents of biological systems. Such constituents could have the character of molecules or aggregates of molecules or they could consist of organized bio-systems such as whole cells, subcellular particles or virus particles.

A chromatographic procedure is governed by a complicated set of interactions between an immobile phase or system of phases and the components of a mobile phase whereby the driving forces behind these interactions arise from electrostatic, hydrogen bonding, charge transfer or hydrophobic phenomena.

Very specific sorptive effects are obtained when one component in a system naturally involved in association-dissociation equilibria is immobilized through fixation to a carrier polymer and the obtained chromatographic medium is used for adsorption of complementary structures. One method based on this principle has been referred to as bioaffinity chromatography.

Covalent binding has rarely been the effect relied upon for the adsorption and chromatography of biochemicals. Its use would imply specificity, i.e. reactivity towards a particular functional group or structure. An enhanced degree of specificity can be anticipated in work with complex biochemicals since in such molecules the reactivity of one and the same functional group often varies due to the sterically induced microenvironment.

A rational approach to the preparation of more or less specific adsorbents for biochemical separations often presents great difficulties. A reasonable starting material would be a chemically neutral, strongly hydrophobic carrier polymer which is permeable to macromolecules. The polymer backbone should itself be chemically inert but equipped with such derivative-forming groups which lend themselves to a wide range of reactions under mild aqueous conditions such as e.g., salt formation, complex formation, redox reactions, substitution and addition reactions as well as radical reactions. The derivative-forming group can then serve as a center for adsorption as it stands or undergoes suitable chemical modification such that the binding bridge might constitute the center of interaction.

A suitable and final derivatization can also take place whereby the introduced substituents or groups contained therein might serve as centers of interaction.

Thiols are functional groups of particular interest from a preparative point of view, which engage in a multitude of reactions even in aqueous systems under mild conditions. Through different mechanisms the thiol group may take part in reactions involving substitution, addition and oxidation as well as complex and salt formation. The product resulting from such reactions would contain bonds of the type S—C, S—S, S—O, S—M, S-metal and S-metal-C. It should be stressed at this point that the thiol group easily undergoes reactions involving radical mechanisms. Agarose gels, particularly in beaded form, have served an important role as carrier polymers within the technique of biochemical separations. Recent years have seen a fast development of biospecific affinity chromatography. This technique has been almost exclusively based on beaded agarose gels, and one has often found it useful to install the center for chromatographic interaction at the end of an arm or a spacer, thereby ensuring a certain minimal distance from the polymer backbone of the carrier.

Other hydrophilic, hydroxyl-containing polymers such as cross-linked dextran have also found certain use in this connection. Thiol groups containing agarose gels have been prepared by Cuatrecasas, J. Biol. Chem., 245, 3059 (1070), from ω-alkyl derivatives of agarose through reaction with acetylhomocystine-thiolactone. The thiolated products were, after further chemical modification, used as adsorbents for bioaffinity chromatography.

Brocklehurst et al., Biochem. J. 133, 573 (1973) have prepared a thiolated agarose gel through direct coupling of glutathione to a cyanogen bromide-activated agarose gel without protection of the thiol group. Eldjarn et al., Acta chem. Scand., 17, 2610 (1963) prepared thiol-containing gels from epichlorohydrin cross-linked dextran through a two-step reaction involving the introduction of amino groups through treatment with aminoethyl sulphate followed by reaction with acetylhomocysteine thiolactone. The resulting thiolated gels were then treated with a bifunctional mercuric reagent, and the resulting product was used to isolate thiol-containing proteins from those without such groups.

Agar and agarose derivatives containing side chains with terminal structures such as —(CH(OH)—CH$_2$—SH, —CH(SH)—CH$_2$OH, —CH$_2$—CH$_2$SH, —CH(SH)—CH$_3$, or —CH(SH)—CH$_2$SH can be prepared from beaded agar and agarose gels without destruction of the gel network.

The beaded starting material is first treated in a well-known manner with epihalohydrins, 2,3-dihalopropanols, bifunctional oxiranes, divinylsulphones or an allyl halogenide with subsequent halogenation to a dihalo-propylether. See reaction formulae 1, 2, 3 and 4 below. The resulting reactive derivatives are then treated with an aqueous solution of NaSH or Na$_2$S$_2$O$_3$. In the latter case this is followed by exposure to a suitable reducing agent such as 1,4-dimercaptobutane or its derivatives. Threo- or erythro-1,4-dimercapto-2,3-butanediol have proved to be advantageous. These latter derivatives will be referred to below as dithiothreitol and dithioerythriol respectively. Use of epihalodrin, dihalopropanol or allylhalogenide involves bridging between the polmer network and the above-mentioned terminal structure through an —O—CH$_2$-linkage. Coupling of suitable long-chain bifunctional oxiranes is one way to directly introduce an arm or spacer effect. The final derivative will then contain long-chain substituents such as —O—CH$_2$—CH(OH)—CH$_2$—O—allyl—O—CH$_2$-terminal group. Divinylsulphone will give rise to linkages with —O—CH$_2$—CH$_2$—SO$_2$-terminal groups. C-alkylated terminal structures can be obtained through the use of a suitable C-alkyl containing epihalohydrin, dihalopropanol, bisoxirane, vinylsulphone or allyl-halide.

These reactions might also be carried out on other hydrophilic hydroxyl-containing polymers such as polyvinylalcohol, partially hydrolysed copolymer of polyvinylchloride-polyvinylacetate, cellulose or epichlorohydrin cross-linked dextran (e.g. Sephadex /registered trademark/ from Pharmacia Fine Chemicals, Uppsala). Amino groups containing polymers such as amino-substituted polyacrylamides also lend themselves to the above reactions.

In certain cases it is desirable that the polymer be permeable, as it would be in gel form; in other cases this is not a desirable feature. For maximal protection against oxidation reactions the thiolated product is generally stored and marketed either as the primarily formed thiosulphate or as a disulphide, —S—S, formed through partial oxidation. These products are then most simply reduced into their active form by treatment with a solution of dithiothreitol. Such a reduction should be a suitable treatment also for thiol-containing polymers after extended periods of storage.

The thio gels can be alkylated at or around pH 7, e.g. through treatment with iodoacetamide and 2,4-dinitrofluorobenzene. Addition of a thiol to a C=C double bond also leads to a thioether structure.

The nucleophilic addition is normally sluggish, but many biological compounds contain double bonds which are activated through conjugation or through the effects of vicinal groups. Sulphur adducts are hence obtainable from α,β-unsaturated aldehydes, ketones, lactones, nitriles and ethers. Quinoid structures are present in certain natural products, and the addition of thiols to quinones constitutes an interesting set of reactions. The thioether structures can be considered stable under most chromatographic conditions.

Reactions of the types described above, which lead to the formation of stable thioethers, make the thiol gels particularly well suited for special preparations of such compounds as biospecific adsorbents, adsorbents for hydrophobic affinity chromatography, and adsorbents based on charge-transfer effects. The thiol gels are also highly useful as starting materials for the introduction of new chemically reactive functional groups for chemisorption, covalent chromatography, chemical immobilization and modification.

Addition and condensation of thiols to aldehydes and ketones result in the formation of hemimercaptals, mercaptals, hemimercaptols and mercaptols whose formation constitutes a plausible mechanism for reversible chemisorption.

The different modes of preparation of thiosulphate and thiol polymers respectively are illustrated by the following reaction formulae:

Reaction scheme 1a

Preparation of thiol-agarose from epichlorohydrin and sodium hydrogensulphide.

Reaction scheme 1b

Preparation of thiopolymer from epichlorohydrin and thiosulphate.

Reaction scheme 2

Preparation of thiol-agarose by means of 1,4-butanediol-diglycidylether, sodium thiosulphate and dithiothreitol (DTT). The thiosulphate containing polymer can be recovered and marketed as a storage safe product which might then be readily converted into a thiol polymer or used to prepare a reactive polymer for fixation of thiol containing compounds (see below).

Reaction scheme 3

Preparation of thiol-agarose from divinyl sulphone, sodium thiosulphate, and dithiothreitol (DTT).

Reaction scheme 4

Preparation of thiol-agarose from allylbromide, bromine, sodium thiosulphate, and dithiothreitol.

Other thio-compounds of interest in this context include thioesters of carbonic acids, which can be synthesized with conventional techniques. These compounds differ markedly from the corresponding alcoholic esters in many respects. Their use in connection with chromatography has not yet been fully explored. Thioesters play an important role in biological systems. They are among other things compounds of high energy. Also they are good reagents for acylation, and the structures activate the α-carbon of the acryl group. Immobilized thioesters are hence of potential interest in different biotechnical contexts, for example as water insoluble reagents for acylation of proteins.

Of great interest is the ease with which thiols undergo oxidation. Of the many products from such a reaction the disulphides play a particularly important role. Their reactivity is generally low in comparison with that of the thiol group. Still they participate in reduction and exchange reactions even under physiological conditions. Reduction of a disulphide can be effected by a thiol group (the thiol-disulphide exchange is indeed a reaction of utmost importance in biological systems).

Reduction of —S—S— bonds by means of polymer bound thiol groups requires a very heavily substituted thiol polymer. Such a polymer can then be used to convert disulphide proteins into thiol proteins, after which reaction the polymer itself will contain disulphide bridges that can be reconverted into thiol groups, for example through treatment with the above-mentioned reducing agent, dithiothreitol.

Enzymes often contain thiol groups which in many cases are directly associated with their activity. Certain plasma proteins such as albumin and ceruloplasmin also contain thiol groups. Subcellular particles do contain protein bound thiol groups as well as other types of thiols. Most proteins however contain —S—S— bridges which are easily converted into thiols by treatment with suitable highly substituted thiol polymers of the kind described in this application.

Thiol polymers can, on the other hand, easily be transformed into polymers with disulphide groups of high reactivity in thiol-disulphide exchange reactions. If such a polymer is allowed to react with a thiol-containing protein, the resulting product is an —S—S— protein polymer. It is however possible, as will be shown below, to activate a thiol polymer even in other ways in order to make it readily available for fixation of thiol containing compounds.

Thiol polymers can be used either directly or after transformation of their thiol groups into suitable disulphides or other similar structures for chemisorption of natural products, for example in protein separations.

Disulphide polymers which lead to a quick and complete reaction with a thiol component in solution are here referred to as "reactive" polymer disulphide structures. In principle such structures can be internal, in which case the enhanced reactivity could be explained by conformational strain, in particular ring tension. In the more important case of external structures such as polymer —S—S—L, the group derives its reactivity from the ligand, L.

In order to drive the reaction as far as possible toward a complete transformation of thiol groups into disulphide groups there are certain requirements on the ligand L which must be fulfilled. Upon cleavage of the —S—S bond, the sulphur which is linked to L has to attain a state of low nucleophilicity, either through tautomerism or resonance, to properly carry out the thioldisulphide exchange.

As an example of —S—S— compounds fulfilling these requirements one might select the class of mixed disulphides formed by an SH-polymer and a compound L—SH, which exists in equilibrium with its thione form and where the latter is the favored species (LSH ⇌ L— = S + $H^{30}$) 2-thiopyridone would constitute an L of this kind. Another example is furnished by —S—S— structures obtained from a thiol-polymer and a derivative of dithiocarbonic acid. In this case a resonance structure might be the underlying cause for the irreversibility of the cleavage reaction. Tetramethylthiuram disulphide forms a good example of this type of mechanism.

Such ligand containing thiol polymers can be prepared from the original thiol polymer through a thioldisulphide exchange with L—S—S—L, whereby the reaction can be controlled so as to give practically stoichiometric conversion of gel-bound thiol groups, leading to compounds of the type polymer, Polymer—S—S—L.

In analogy with the above, the nature of the ligand L influences the "driving force" behind the reaction between a polymer—S—S—L compound and a thiol compound in solution.

We have, however, found that the introduction of ligands into a thiol polymer can occur directly through treatment of the thio-sulphate ester polymer with an L—S—S—L reagent, i.e. without prior reduction of the thiosulphate ester into thiol. This is of considerable technical and economical advantage since it justifies the use of the storage-stable thiosulphate polymer which in one single step is converted with almost the theoretical yield into the strongly reactive polymer—S—S—L product. This may, for example, be accomplished by reaction with one of the above-mentioned disulphide compounds.

A completely different way to create polymer disulphide ligands of the type discussed here, i.e. other type polymer—S—S—prot compounds (prot = protein), has its basis in the reaction between a polymer sulphenyl derivative and a protein-thiol. Such a sulphenyl derivative can be obtained for example through the reaction between a polymer-thiol and an azodicarboxylate according to the general formula 1. The subsequent reaction with the protein-thiol is illustrated in formula 2.

The ethylcarboxylate groups might be replaced by other carboxylate groups or more generally by other electron-attracting groups.

The immobilization of a thiol-protein consequently proceeds through a two-step reaction, which as step number one involves the activation-transformation of the thiol-polymer into an alkylsulphenylhydrazide. This compound is stable upon storage in aqueous medium and reacts under mild conditions such as weakly acidic solution of pH 4 or lower, with a thiol compound in solution yielding a polymer—S—S—Prot or other analogous product. In the above discussions HS—Prot has been used as an example of a thiol compound which lends itself to coupling. This must not be interpreted as a limitation since the process can be carried out with any soluble thiol compound as well as with species such as cellular fragments, virus particles etc. provided their surfaces contain accessible SH-groups either naturally occurring or artificially introduced.

The development of techniques for biospecific chromatography within the field of biochemistry has largely been paralleled by the development of water-insoluble enzymes. The most commonly used methods for immobilizing enzymes involve their covalent attachment or adsorption to a polymer carrier. Of special interest in the current context would be the possibility for immobilizing enzymes via a disulphide bridge. The binding lends itself to reductive cleavage under suitable conditions. A column of immobilized enzyme, which after a certain period of use has lost its activity, can hence be regenerated in situ through reductive elimination of inactivated enzyme. After reactivation of the polymer (still in situ), the column reactor is then ready for renewed coupling of fresh enzyme.

Another method for reversible immobilization of enzymes, which has found use lately, has its basis in the hydrophobic interaction between an enzyme and a carrier polymer with mixed hydrophobic-hydrophilic characteristics. Such a technique for immobilization does not possess considerable advantages since it permits removal of the enzyme, following partial or complete inactivation, through changes in ionic strength or other environmental parameters (see for example Swedish Patent Application No. 7410550-3).

This removal can at times be problematic. In such cases there exists the possibility of attaching the hydrophobic structure, originating for example from an alkylmercaptane, to the hydrophilic polymer by means of a disulphide bridge.

The release of enzymic protein would then take place upon reduction of the disulphide bridge which causes a rejection of the composite enzyme-alkyl structure.

It does, however, seem possible to codify the reactions above in the following manner.

Firstly a reactive polymer derivative has to be prepared which has the general formula $\textcircled{P}$—S—Y, where $\textcircled{P}$—S originates from the polymers P—SH or PS—SO$_3$.Na with which this application is concerned. The symbol Y denotes a group such that through the reaction, $\textcircled{P}$—S—Y + HS—Prot $\rightleftarrows$ $\textcircled{P}$—S—S—Prot + Z, a product Z is formed which under the prevailing reaction conditions has no appreciable capacity to drive the reaction in the opposite direction (HS—Prot symbolizes a thiol-containing organic compound, for example a protein or a particle with exposed SH-groups). The Y-group can fulfill these demands in at least two different ways:

a. Certain disulphides of type A—S—S—A have the capacity to react with a thiosulphate or thiol polymer leading to the formation of a reactive disulphide polymer according to the general formula (1)

$$\textcircled{P}\text{—SH} + \text{A—S—S—A} \rightleftarrows \textcircled{P}\text{—S—S—A} + Z'. \qquad (1)$$

Z will immediately establish a thione-thiol equilibrium in which the thione is the strongly favored species. Instead of a P—SH polymer the corresponding thiosulphate polymer PS—SO$_3$Na might be used directly (2).

where Z" symbolizes soluble reaction products which, like Z, do not stimulate the reverse reaction.

Reactions between the reactive disulphide polymer and a dissolved thiol compound, such as a thiol containing protein, will then take place according to the formula $$\textcircled{P}\text{—S—S—A} + \text{HS—Prot} \rightarrow \textcircled{P}\text{—S—S—Prot} + Z.$$

The resulting polymer-protein product can then according to the above be split into $\textcircled{P}$—SH + Prot-residue, upon treatment with a suitable reducing agent.

b. Upon contact with a thiol polymer azodicarboxylate of the formula $R_1-N=N-R_1$ gives rise to a product which, due to the electron attracting properties of $R_1$, shows a high reactivity towards thiol containing compounds.

The activated polymer can then react with HS—Prot to form ⓟ—S—S—Prot + $R_1$—NH—NH—$R_1$, where the soluble hydrazide has no tendency to drive the reaction backwards.

Remarkably enough the activated polymers of both kinds can, in spite of their reactivity, be recovered, washed and stored without noticeable reduction in activity. The coupling reaction itself, i.e. the actual immobilization of, for example, ann HS—Prot, can consequently be carried out at a later point in time.

One can reduce enzymes which lack thiol groups but contain disulphide structures by means of a highly substituted thiol gel. The resulting thiol groups can subsequently be used for the immobilization. Through the use of suitable reagents for thiolation one might also introduce thiol groups into the enzyme which would then have the proper form to react as "HS—Prot" in the schemes above.

Reactions with polymer-bound thiol groups which lead to stable thioether structures can also be of use for the immobilization of enzymes. The polymer could through such a reaction be provided with new reactive groups which are directly or by means of a suitable reagent capable of forming a covalent bond with some functional group in the enzyme molecule. Alternatively centers for enzymic adsorption may be introduced as thioethers.

Besides the actual immobilization reaction there are other factors which influence the immobilization of an enzyme. It can often be of importance to provide the polymer network with such functional groups which will enhance the stability of the enzyme. Furthermore, constituents of a substrate-product inhibitor system might be influenced by a polymer substituent so as to give an increase in catalytic activity under a given set of conditions. Since reactions with thiol gels occur under very mild conditions in aqueous medium, such supplementary substitution reactions might be carried out even after the process of immobilization.

Analogous methods can be used to immobilize microorganisms, cells, subcellular particles, membraneous fragments, receptor sites etc.

The thiol polymers described here can be used in a variety of biological contexts. Their capacity to form metal complexes and their electron exchange properties might consequently be relied upon to protect thiol-containing biological systems from auto-oxidation.

In this case the biological system would be stored in the presence of a thiol gel. Auto-oxidation of thiol is known to be catalyzed by certain metal ions such as $CU^{2+}$ as well as by the product of oxidation, i.e. the disulphide. A continuous exchange of electrons between the produced disulphide and the thiol gel keeps the thiol concentration in the solution at a constant level until the electron exchanger is used up.

The thiol polymers can also be used as a supporting phase for the chemical modification of natural products. In such a case the attachment to the polymer occurs via a disulphide bridge which is hydrolytically stable but which after the desired modification reactions lends itself to reductive cleavage. Since natural products often are polyfunctional in nature, their reactions, when carried out in a homogeneous phase, often lead to intermolecular cross-linking. Such undesired side reactions could be avoided if the modification reaction were to take place in a polymer phase.

Another possible use for the reductive disulphide cleavage under mild conditions lies in the attachment of one of the components in a biological association-dissociation complex by means of a disulphide bridge. A reduction step would then release the entire complex of adsorbate and ligand. This is of special interest when a specific association-dissociation complex is formed by a heterofunctional molecule such that the complex formation does not impair a certain biological activity under observation.

Many metal ions and metal-organic compounds form more or less stable complexes with the thiol gels described here. These thiol gels can consequently be used as water-insoluble complexing agents or as media for chromatography of metal containing proteins, whereby the differential tendency for complex formation would be the major cause for separation.

The invention is further illustrated by the experimental examples below as well as by two diagrams in which.

Figure 1:
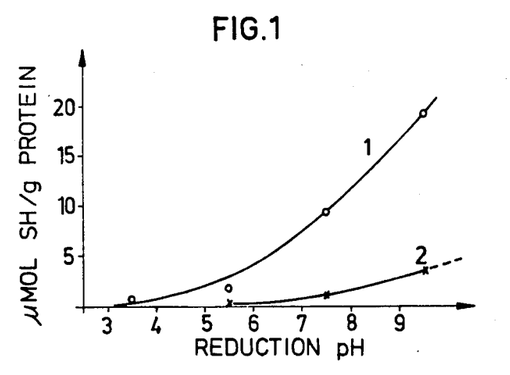
FIG. 1 shows the reduction of amylglucosidase by thiol agarose gel as a function of pH.

In FIG. 1 curve 1* discloses the SH content immediately after the reduction step and curve 2* the SH content 2 hours after the reduction step.

Figure 2:
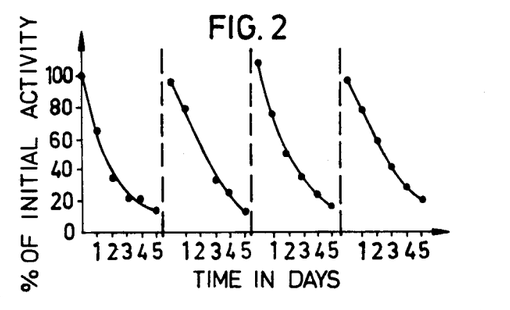
FIG. 2 shows the regenerability of a column packed with activated thiol agarose gel.

In FIG. 2 the activity of the gel is shown as % of the initial activity as a function of the time in days in repeated regenerations.

I. PREPARATION OF OXIRANE-ACTIVATED AGAROSE GELS OF VARYING DEGREE OF SUBSTITUTION WITH RESPECT TO OXIRANE STRUCTURES a. With Epichlorohydrin 3 g of washed and suction dried agarose gel in bead form, 2-6% agarose, was suspended in 2.4 ml of 1 M sodium hydroxide solution. Dropwise addition of epichlorohydrin took place at room temperature under stirring. The temperature was then raised to 60° C and the reaction mixture was stirred for 2 hours. The gel was washed on a glass filter with water until neutral reaction. Results are presented in Table 1.

b. With 2,3-Dibromopropanol

The experiments were carried out in analogy with the description under (a).

c. With 1,4-Butanediol-diglycidyl-ether 3g of washed, suction dried agarose gel in bead form, 2-6% agarose, was suspended in 1.5 ml of 2.5 M sodium hydroxide solution followed by the addition of 12 mg sodium borohydride. The bisepoxide was added dropwise under vigorous stirring. The reaction time was 6 hours at room temperature, whereupon the gel was washed on a glass filter with water until neutral reaction, then with 20 ml acetone, and finally with water until the acetone was completely eliminated.

d. With 1,3-Butanediol-diglycidyl-ether

The experiments were carried out according to the description under (c).

e. Quantization of Gel Bound Oxirane Structures

A gel portion, containing of the order 10–100 μequiv. of oxirane structures, was washed and suspended in 10 ml of distilled water. The pH of the suspension was adjusted to 7.00, whereupon 1.00 ml thereof was transferred to a titration vessel with a plastic pipet. At the moment of sampling the suspension was vigorously stirred by a magnetic rod, 1.00 ml of a 2 M sodium thiosulfate solution at pH 7.00 was added to the suspension, after which a continuous titration with 50 mM hydrochloric acid in a pH-stat was carried out. The titration time was 30–120 minutes depending on the oxirane content of the gel. The suspension was stirred vigorously by a magnetic rod during the entire titration. The dry content of the gel suspension was determined from 5.0 ml samples of the suspension, which were washed on a glass filter first with mixtures of acetone and water, subsequently with pure acetone, and dried for 24 hours at 100° C over phosphorous pentoxide.

II. PREPARATION OF DIVINYLSULPHONE ACTIVATED AGAROSE GELS OF VARYING DEGREE OF SUBSTITUTION WITH RESPECT TO VINYLSULPHONE STRUCTURES

Sepharose ® 6B, a beaded agarose gel, containing ca. 6% polysaccharide, from Pharmacia Fine Chemicals, Uppsala, was washed on a glass filter and dried by suction; 10 g of this agarose gel was suspended in 10 ml of 0.5 M sodium carbonate solution at pH 11, whereupon the divinylsulphone was added and the system was allowed to react for 70 minutes under stirring. The reaction product was washed with water on a glass filter and subsequently analysed for vinylsulphone structures through reaction with an excess sodium thiosulphate followed by titration of resulting OH-ions with hydrochloric acid in the same manner as described under heading I (e). The results for varying amounts of divinylsulphone are presented in table 2.

III. PREPARATION OF 2,3-DIBROMOPROPYLETHER-AGAROSE GELS WITH VARYING DEGREE OF SUBSTITUTION 100 ml agarose gel, beaded, epichlorohydrin crosslinked, prepared in the customary way and containing ca. 6% polysaccharide was washed, dried through suction, and mixed with 100 ml 5 M sodium hydroxide solution containing 500 mg sodium borohydride, whereupon a portion of allylbromide was added to the suspension.

The reaction mixture was heated to 70° C for 4 hours under vigorous stirring and reflux condensation.

After the reaction the gel was washed on a glass filter first with mixtures of alcohol and water, subsequently with 96% ethanol and then with carbon tetrachloride. The gel was suspended in 100 ml of carbon tetrachloride, and bromine was added until a visible bromine coloration persisted. Results of the experiments are presented in table 3.

IV. PREPARATION OF "BUNTE SALZ"-AGAROSE GELS WITH VARYING DEGREES OF SUBSTITUTION a. Preparation of "Bunte Salz"-AGAROSE gels from Epichlorohydrin, 2,3-Dibromopropanol, 1,4-Butanediol-diglycidylether and 1,3-Butanediol-diglycidylether Activated Agarose Gels 3 g each of suction dried gel preparation from I (a), I (b), I (c) and I (d) was washed with 0.5 M sodium phosphate buffer at pH 6.25. The gel was again suction dried, whereupon it was suspended in 3 ml of the above-mentioned phosphate buffer to which was later added 3 ml of a 2 M sodium thiosulphate solution. The reaction mixture was shaken for 6 hours at room temperature and the product then washed with water. Such a product is referred to as "Bunte Salz" gel. Sulphur analyses are given in table 1.

b. Preparation of "Bunte Salz" Agarose Gels from Dinvinylsulphone Activated Agarose Gels The preparations are carried out in a manner analogous to the preparation from epoxide activated gels according to (a), and the sulphur analyses are reported in table 2.

c. Preparation of "Bunte Salz" Agarose Gels from 2,3-Dibromopropylether Agarose Gels 5 g of 2,3-dibromopropylether agarose, which had been suction dried after washing with distilled water, was suspended in a solution of 3.75 g $Na_2S_2O_3 \cdot 5H_2O$ dissolved in 5 ml of water. The mixture was allowed to react for 5 hours at 95° C, after which the gel was washed with water on a glass filter until elimination of salt. Results of sulphur analyses are given in table 3.

V. PREPARATION OF THIOL AGAROSE GELS OF VARYING DEGREE OF SUBSTITUTION WITH RESPECT TO THIOL STRUCTURES THROUGH REDUCTION OF "BUNTE SALZ" GELS WITH DITHIOTHREITOL a. From "Bunte Salz" Gels Obtained through Reaction with Epichlorohydrin, 2,3 -Dibromopropanol, 1,4-Butanediol-diglycidylether and 1,3-Butanediol-diglycidylether "Bunte Salz" gel was washed with water on a glass filter and dried by suction; 3 g of gel was suspended in 0.3 M sodium bicarbonate solution to a total volume of 6 ml. The amount of reducing agent (dithiothreitol) needed for the reaction was calculated based on the above-described method for oxirane analysis, and the agent was then added in at least double excess.

The dithiothreitol was dissolved in 3 ml of a 1 mM EDTA solution and allowed to react at room temperature for 30 minutes with stirring. The product was washed on a glass filter with 30 ml of a 0.1 M sodium bicarbonate solution which was 1 M with respect to sodium chloride and 1 mM with respect to EDTA, and finally washed with 100 ml of a 1 MM EDTA solution.

The degree of substitution of thiol groups was determined through a reaction with 2,2′-dipyridyl-disulphide according to Brocklehurst et al., Biochem. J. 133, 573 (1973). Their procedure was modified in that 0.1 M sodium bicarbonate solution was used instead of tris-buffer. Results of elemental sulphur analysis are displayed in table 1.

In table 1 is presented a collection of results from thiolations of 6% agarose gel, where the agarose beads have been activated to varying degrees through reaction with epichlorohydrin, 2,3-dibromopropanol, 1,4-butanediol-diglycidylether and 1,3-butanediol-diglycidylether.

The oxirane group containing gel has been treated with sodium thiosulphate solution and the resulting "Bunte Salz" gel subsequently reduced with dithiothreitol. The sulphur content of the "Bunte Salz" gel and the thiol gel have been determined and the thiol content of the latter has been quantitated through the 2,2'-dipyridyldisulphide reaction.

Table 1

| Oxirane activation ml of reagent/ 3 g gel | "Bunte Salz" gel μmoles S/g dry product | Thiol gel μmoles S/g dry product | Thiol gel μequiv. thiol group/g dry product |
| --- | --- | --- | --- |
| Epichlorohydrin 0.45 | 1260 | 690 | 660 |
| Epichlorohydrin 0.15 | 340 | 220 | 170 |
| Epichlorohydrin 0.075 | 70 | 55 | 50 |
| 1,4-butanediol-diglycidylether 5 | 1500 | 850 | 860 |
| 1,4-butanediol-diglycidylether 1.2 | 740 | 370 | 410 |
| 1,4-butanediol-diglycidylether 0.3 | 240 | 105 | 110 |
| 1,3-butanediol-diglycidylether 1.2 | 690 | 350 | 390 |
| 2,3-dibromopropanol 0.3 | 900 | — | 440 | b. From "Bunte Salz" Gels Obtained from Divinylsulphone Activated Agarose Gels The reduction with dithiothreitol was carried out in a manner analogous to the procedure described under (a). Table 2 presents the results of thiolations of 6% agarose gels treated with divinylsulphone so as to obtain a variety of degrees of substitution with respect to vinylsulphone structures. The activated gels have been treated with sodium thiosulphate solutions and the resulting "Bunte Salz" gels subsequently reduced through reaction with dithiothreitol.

Table 2

| Activation with divinylsulphone (DVS) ml DVS/10 g agarose gel | Vinylsulphone content | | Thiol content μequiv./g dry product |
| --- | --- | --- | --- |
| | μequiv./g gel | μequiv./g dry product | |
| 0.05 | 7.4 | 170 | 172 |
| 0.1 | 13 | 280 | 282 |
| 0.25 | 28 | 610 | 526 |
| 0.5 | 43 | 900 | 825 |
| 1.0 | 64 | 1260 | 1080 | c. From "Bunte Salz" Gels Obtained out of 2,3-Dibromopropylether Agarose Gels The reduction with dithiothreitol was carried out as described under (a) with the modifications that a 3-fold excess of reagent, based on bromine analysis, was used and that the reaction time was extended to 1 hour.

Results of analyses for bromine-, sulphur- and thiol-content are presented in table 3 for the case of thiolation of 6% agarose gel previously cross-linked with epichlorohydrin. The cross-linked agarose beads are treated with allyl bromide to various degrees of substitution with respect to allylether structures. The allylether gel is treated with bromine, and the 2,3-dibromopropylether gel treated with sodium thiosulphate solution, whereupon the resulting "Bunte Salz" gel is reduced with dithiothreitol.

Table 3

| Reaction with allyl bromide ml reagent/ 100 ml gel | 2,3-dibromo-propylether agarose mmoles Br/g dry product | Thiol agarose mequiv. thiol group/g dry product | Thiol agarose mmoles Br/g dry product |
| --- | --- | --- | --- |
| 20 | 3.5 | 2.1 | |
| 10 | 2.0 | 1.5 | |
| 5 | 0.9 | 0.7 | 0.15 |
| 2 | 0.5 | 0.4 | |

VI. PREPARATION OF THIOL AGAROSE GELS OUT OF OXIRANE ACTIVATED AGAROSE GELS USING SODIUM SULPHIDE

First 3 g of washed and suction dried 6% agarose gel were suspended in 2.4 ml of 1 M sodium hydroxide. Then 0.35 ml of epichlorohydrin were added, whereupon the treatment followed the procedural description under 1(a). The oxirane content of the product was determined to be 850 μequiv./g dry product.

$Na_2S . 9H_2O$ (Merck, Darmstadt) was used to prepare a 1 M aqueous sodium sulphide solution of which a 15 ml portion was allowed to react with 3 g of oxirane gel for two hours under stirring. The resulting thiol content amounted to 410 μequiv./g dry product.

VII. DERIVATIZATION OF THIOLATED AGAROSE GELS INTO GELS CONTAINING THIOETHER STRUCTURES

In the following experiments use was made of thiolated agarose gel, produced from beaded 6% agarose gel through treatment with epichlorohydrin, sodium thiosulphate and dithiothreitol. The thiol group content was determined to be 650 μequiv./g dry product.

a. Reaction with Iodoacetamide 1 g of gel was suspended in 2 ml of a 0.1 M sodium bicarbonate solution at pH 8.4, which was made 1 mM with respect to EDTA for complex formation with metal ions possibly present in the reaction mixture; 1 ml of ethanol and 15 mg of iodoacetamide were added and the mixture was allowed to react for one hour at room temperature. The resulting product was washed with ethanol, whereupon a nitrogen analysis showed 584 μmoles N/g dry product.

b. Reaction with Dinitrochlorobenzene 1 g of gel was suspended in a mixture consisting of 2 ml 0.1 M sodium bicarbonate solution, which was 1 mM with respect to EDTA, and 2 ml of ethanol. After addition of 15 mg 2,4-dinitrochlorbenzene the mixture was allowed to react for one hour at room temperature. The resulting product was washed with ethanol. Analysis of nitrogen content gave 964 μmoles N/g dry product.

c. Reaction with Vinyl-2-chloroethylether 1 g of gel was suspended in 2 ml of a mixture of 25% ethanol and 75% water. Upon addition of 0.5 ml vinyl-2-chloroethylether the mixture was allowed to react for 2 hours. The resulting product was washed with alcohol and was subsequently subjected to chlorine analysis, which indicated a content of 75 μmoles Cl/g dry product.

d. Reaction with Cinnamic Aldehyde 1 g of gel was suspended in 2 ml water. To the suspension was subsequently added 1 ml ethanol, 0.1 ml triethylamine and 0.1 ml cinnamic aldehyde, and the mixture was allowed to react for 5 hours. After washing with alcohol and water, the product was treated for aldehyde content with Schiff's reagent, which resulted in a strongly positive reaction.

e. Reaction with Acrolein

The reaction was carried out as described under (d) with the exception that 50 μl acrolein was added instead of cinnamic aldehyde. The product gave a positive reaction with Schiff's reagent.

f. Reaction with Benzoquinone 2 g of thiol gel was suspended in 1 ml of 0.2 M sodium acetate buffer at pH 5.6. 32 mg of p-benzoquinone was dissolved in 1 ml of ethanol and mixed with the gel suspension. The reaction took plate at room temperature under stirring for 5 and 20 hours respectively. The products were washed with alcohol-water mixtures.

The coupling potential of the benzoquinone agarose gels was determined as reactivity towards N-acetyl-L-cysteine; 1 g of quinone gel was suspended in 1 ml of acetate buffer at pH 4.5 to which 50 mg of N-acetyl-L-cysteine was subsequently added. After a reaction time of 20 hours at room temperature, the product was carefully washed and dried, whereupon it was submitted to nitrogen analysis.

Since benzoquinone is expected to react with alcohol groups in the gel matrix, a set of experiments was carried out in a manner completely analogous to the procedure described above, this time involving agarose gels without thio groups. The results of N-acetyl-L-cysteine coupling to p-benzoquinone activated agarose and thiol agarose are displayed in table 4.

Table 4

| Polymer | Reaction time (benzoquinone treatment) | % N | N-acetyl-L-cysteine μM/g (computed from N-analysis data) |
|---|---|---|---|
| Agarose | 5 | 0.029 | |
| Agarose | 20 | 0.113 | 70 |
| Thiol agarose | 5 | 0.410 | 280 |
| Thiol agarose | 20 | 0.633 | 440 | g. Reaction with Cortisone 1 g of gel was washed on a glass filter with 90 % aqueous ethanol. The gel was then suspended in 2 ml of this medium and 50 mg of testosterone added to the suspension. The reaction mixture was exposed to γ-irradiation for 15 hours whereupon, after washing, the product was shown to contain 25 mg of substituted cortisone/g dry product.

For comparison an analogous experiment was carried out in which the irradiation procedure was omitted. No uptake of cortisone could be detected.

VIII. USE OF THIOL AGAROSE AS WATER INSOLUBLE COMPLEXING AGENT a. Reaction with p-Chloromercurobenzoic Acid 1 g of thiol agarose was suspended in 0.3 M sodium chloride solution and the pH was adjusted to 7.0. The suspension, having a total volume of 20 ml, was then saturated with $N_2$ gas. A solution of 14.4 mg of p-chloromercurobenzoic acid in 0.3 M sodium chloride was adjusted to pH 7.0 and a volume of 10 ml; 1.0 ml of gel suspension was reacted with 1.0 ml of the reagent solution under continuous addition of a 0.020 M sodium hydroxide solution to maintain a pH of 7.0. The sodium hydroxide consumption amounted to 580 μequiv./g dry product.

b. Reaction with $Cu^{2+}$

A solution of $CuSO_4 . 5H_2$/ in quartz-distilled water was made 0.125 mg/ml with respect to $CU^{2+}$. A column of 0.75 cm$^2$ cross section, containing 3 ml of thiol agarose gel, was washed with distilled water. The thiol agarose had neen prepared with epichlorohydrin, sodium thiosulphate and dithiothreitol and contained 500–700 μequiv. SH-groups/g dry product. $Cu^{2+}$-ions were registered photometrically at 254 nm also through a spot test reaction with a reagent consisting of o-tolidin and ammonium rhodanide in acetone according to F. Feigl, Spot Tests in Inorganic Analysis, 5th ed, p. 84. This reagent is capable of detecting copper in dilutions of the magnitude 1:5 $\times 10^6$.

Copper solution was pumped through the column and not until 25.3 ml had passed could any trace of $Cu^{2+}$ be detected in the eluate by means of the spot test. This corresponds to an absorption of 12.6 mg of $CuSO_4 . 5H_2O$. Adsorbed cupric sulphate can be displayed by EDTA.

c. Activation of Hg-papain

Papain is an enzyme containing one thiol group per molecule; this group is necessary for the enzymatic activity. The enzyme is often stored and delivered as mercuro-papain in which the reactive thiol group is protected through an addition of $HgCl_2$ to the enzyme at the preparation. Mercuro-papain is enzymatically inactive and is normally activated through the addition of a solution containing cycteine and EDTA. Thiolated agarose can be used as an activator for mercuro-papain. The activity of papain prepared in this manner amounts to 80–90% of the value recorded after activation with cysteine-EDTA solution, either when measured against benzoyl-L-arginine ethyl ester or against casein.

IX. USE OF HIGHLY SUBSTITUTED THIOL AGAROSE AS REDUCING AGENT a. Methylene Blue

Methylene blue forms reddish crystals which easily dissolve in water giving a blue color. Upon reaction the solution turns into uncolored leuco-methylene blue.

1 g of thiol agarose corresponding to around 50 μequiv. of thiol groups was suspended (in a test tube) in 3 ml of 0.1 M sodium bicarbonate solution which was made 0.3 M with respect to sodium chloride and 1 mM with respect to EDTA. The suspension was equilibrated with $N_2$-gas and 1 ml (25 mM) of methylene blue was added. Decoloration occurred within 10–15 minutes. The nitrogen flux was kept constant during the reaction.

b. Reduction of Disulphide bond in Chymotrypsin

Chymotrypsin was dissolved in 1 mM HCl to a concentration of 25 mg/ml. A column of bed volume 15.4 ml was packed with highly substituted thiol agarose prepared from 6% agarose through reaction with epichlorohydrin, sodium thiosulphate and dithiotreitol. The degree of substitution of thiol groups was around 800 μequiv./g dry product. 1 ml of the chymotrypsin solution was mixed into 1 ml of a 0.1 M sodium bicarbonate solution, 1 mM with respect to EDTA, and subsequently pumped through the thiol agarose column at a flow rate of 15 ml/h. Chymotrypsin eluting from the column was reacted with iodoacetic acid in excess and the reaction mixture desalted through gel filtration on Sephadex G-10 from Pharmacia Fine Chemicals, Uppsala. Iodoacetic acid reacts with thiol groups, and the thioether carbonic acid of cysteine can be quantitatively determined through amino acid analysis following acid hydrolysis. Unreduced chymotrypsin was also reacted with iodoacetic acid with subsequent gel filtration on Sephadex G-10 and amino acid analysis. The results are presented in the table below.

|  | Content of 8-carboxymethylcysteine, μequiv./25 mg protein |
|---|---|
| Chymotrypsin | 0 |
| Reduced chymotrypsin | 2.5 | c. Reduction of Amyloglycosidase 2.7 ml of highly substituted thiol agarose, the same preparation as used in (b), was transferred to a column with an inner diameter of 18 mm. Solutions of amyloglycosidase, Sigma Grade II, at a concentration of 0.1% w/v, were prepared from the following buffer systems:

| 50 mM sodium acetate | pH 3.5 |
| 50 mM sodium phosphate | pH 5.5 |
| 50 mM sodium phosphate | pH 7.5 |
| 50 mM sodium bicarbonate | pH 9.5 |

All solutions were then made 1 mM with respect to EDTA and saturated with $N_2$-gas. The enzyme solutions were passed through the reducing column at a flow rate of 10 ml/h. Four samples, each of 2.5 ml, were taken and analysed for content of SH-groups with 2,2'-dipyridyldisulphide. Two of the samples served as blanks. Determinations of thiol content were made immediately and after 2 hours. The results, given in the diagram of FIG. 1, demonstrate the pH-dependence of the thiol agarose mediated reduction of amyloglucosidase.

The thiol content of the reduced enzyme was determined directly after passage through the column, as well as 2 hours later.

X. IMMOBILIZATION OF ENZYMES THROUGH FIXATION OF THIOL AGAROSE BY MEANS OF THIOL-DISULPHIDE EXCHANGE REACTIONS a. Preparation of 2-Pyridine Disulphide Agarose

Beaded 2% agarose gel was cross-linked with epichlorohydrine; 180 g of washed and suction dried gel was suspended in 142 ml of 1 M sodium hydroxide solution followed by an addition of 5 ml epihlorohydrin. The reaction time was 1 hour at 60° C. The gel was then washed and suspended in 180 ml of 0.5 M phosphate buffer (20.5 g $NaH_2PO_4.H_2O$, 14.0 g $Na_2HPO_4.2H_2O$ in 0.5 1 solution). 180 ml of a 2 M sodium thiosulphate solution was added to the suspension and the mixture was left to react at room temperature for 6 hours. The resulting product was washed with water and reduced by 216 mg dithiothreitil dissolved in 180 ml of a 0.1 M sodium bicarbonate solution made 1 mM with respect to EDTA. The product was washed with 1 M sodium chloride solution, 1 mM with respect to EDTA, then with a 1 mM EDTA solution and finally with 50% aqueous acetone; 4 g of pyridine disulphide was dissolved in 180 ml of 50% aqueous acetone, mixed with the gel, and reacted for 30 minutes at room temperature. The resulting product was washed on a glass filter with 50% aqueous acetone and finally with 1 mM EDTA solution. Analyses showed the oxirane content after treatment with epichlorohydrin to be 80 μequiv./g dry product; the content of 2-pyridine disulphide structures amounted to 50 μequiv./g dry product as determined by N-analysis.

The coupling column was shown to have adsorbed an activity corresponding to 0.32 enzymic units/mg conjugate. The amount of amylglucosidase activity pumped into the column was 80 units, corresponding to 1,25 units/mg dry gel. The activity of the amyloglycosidase was determined against starch using the 3,5-dinitrosalicyclic acid reagent described by Bernfeld in Methods in Enzymology, Vol. 1, AP, New York, 1955, p. 149.

The enzymic activity was determined from a standard curve based on glucose, and the enzymic unit was defined as the amount of glucose (mg) formed in a 3- b. Immobilization of Amyloglucosidase

Amyloglucosidase was reduced by a highly substituted thiol agarose in the manner described under IX(c). The reducing column was 11 cm in length and contained 17 ml of thiol agarose prepared from 2% agarose with epichlorohydrin, sodium thiosulphate and dithiominute period.

During a control experiment 2 ml of the amyloglucosidase solution was pumped directly into a column of pyridine disulphide agarose without previous passage through the reducing column. The washing procedure was carried out as described above. No activity was adsorbed onto the pyridine disulphide column.

hreitol. The degree of substitution was ca. 750 μequiv./g dry product. In direct connection with the reducing column was installed a coupling column with an inner diameter of 2.1 cm containing 3.2 ml of 2-pyridine disulphide agarose prepared according to (a) above.

A solution of 41.4 mg amyloglucosidase in 6 ml of 0.1 M sodium bicarbonate solution, made 1 mM with respect to EDTA, was prepared, out of which a 2 ml portion was taken and pumped through the reduction column and also through the subsequent coupling column at a flow rate of 10.7 ml/h. The coupling column was then washed at the same flow rate with the following solutions in the indicated order and durations:

| | | |
|---|---|---|
| 0.1 M sodium bicarbonate solution/1 mM EDTA | 2 hours | |
| 0.1 M sodium acetate solution, pH 4.8 | 15 hours | |
| 0.5 M sodium acetate solution, 1% with respect to starch | 3 hours | |
| 0.01 M sodium acetate solution, pH 4.8 | 3 hours | | c. Immobilization of α-Amylase

The immobilization reaction between an enzyme and a thiol gel can also be carried out after an organic chemical introduction of thiol groups into the enzyme molecule for the subsequent use as binding sites. The introduction of thiol structures into proteins can take place, for example, through a reaction with methyl-3-mercaptopropionimidate.

0.1–1.0 ml of α-amylase suspension, Sigma type IA, 25 mg/ml, was dissolved in 5 ml of 0.1 M sodium bicarbonate solution. The solution was degassed for 10 minutes in an N₂-tent, whereupon 1-3 mg of methyl-5-mercaptopropioimidate was added. After 60 minutes in a nitrogen atmosphere, the mixture was separated through gel filtration on Sephadex G-25 (reg. trademark) in 0.1 M sodium bicarbonate at a flow rate of 60 ml/h, whereby material of low molecular weight was eliminated. Fractions of 20 ml were collected and those containing α-amylase activity were each incubated with a 4 ml portion of 2-pyridinedisulphide agarose previously washed with 0.1 M sodium bicarbonate solution. The mixtures were kept at room temperature under stirring for 6-15 hours and were subsequently washed, first on a glass filter with the coupling buffer, then in a column with a flow of 10 ml/h according to the following pattern:

| | |
|---|---|
| 0.1 M sodium bicarbonate solution, 0.2 M with respect to sodium chloride | 24 hours |
| 0.1 M sodium phosphate buffer, pH 6.9, 0.2 M with respect to sodium chloride and 1% with respect to starch | 24 hours |
| 0.02 M sodium phosphate buffer, pH 6.9, 0.01 M with respect to sodium chloride | 24 hours |

The enzymic conjugates, containing about 1 mg of dry conjugate/ml suspension, were suspended in the latter washing buffer and stored at +4° C.

To 1 ml of a properly diluted α-amylase solution or α-amylase agarose suspension was added 1 ml of a 1% starch solution in 0.02 M sodium phospate buffer pH 6.9, which was 0.01 M with respect to sodium chloride. The amount of reducing sugar formed was determined after 3 minutes' stirring at 23° C through reaction with 3,5-dinitrosalicyclic acid as described above. Maltose was used as standard and the activity data are presented in table 5 which also contains data on coupling of α-amylase. The enzyme, which had been previously thiolated through reaction with methyl-3-thiol-propiomidate, was coupled to thiol agarose activated with 2,2'-pyridine disulphide. The activity was measured against a 1% starch solution.

Table 5

| Catalyst | Enzyme content of conjugate, mg/g | Activity, mg maltose/ mg α-amylase, 3 minutes | Relative activity % |
|---|---|---|---|
| α-amylase | — | 480 | — |
| α-amylase-agarose | 85 | 92 | 19.2 |
| α-amylase-agarose | 24 | 235 | 49 |
| α-amylase-agarose | 18.5 | 205 | 43 |
| α-amylase-agarose | 15 | 225 | 47 |

One of these preparations was used for continuous column conversion of starch at room temperature over a period of 20 days before any decline in activity could be detected.

A rise in operating temperature to 45° C immediately resulted in a decline in activity such that after about 2 days only 50% of the initial activity, and after 5 days practically no activity, remained on the column. The reactor column can, however, be regenerated in situ through percolation with a 20 mM dithiothreitol solution in 0.1 M sodium bicarbonate. This is followed by washing with 0.1 M sodium bicarbonate solution and percolation with 1.5 mM of 2,2'-dipyridyldisulphide dissolved in 0.1 M sodium bicarbonate. A subsequent washing is performed with 0.1 M sodium bicarbonate solution which is 1 M with respect to sodium chloride, and finally, the material is exposed to a solution of thiolated α-amylase. The regenerability is demonstrated by the diagram of FIG. 2, which shows the percent of initial activity as a function of time in days during a series of repeated regenerations of the column.

XI. COVALENT CHROMATOGRAPHY a. Purification of Urease

Urease is a thiol containing enzyme. A solution of 150 mg of urease, Sigma type IV, in 50 ml of 0.1 M Tris-HCl buffer at pH 7.2 was pumped through a column containing 2-pyridine disulphide agarose according to X(a). The height of the gel bed was 22 mm, its diameter 10 mm, and the flow through the bed 5 ml/hour. The column had been conditioned with the Tris-HCl buffer and, after exposure to the urease solution, the column was again washed with the same buffer. The immobilized urease was subsequently released from the gel by a 50 mM solution of dithiothreitol.

After gel filtration of the released enzyme, its specific activity was determined and compared with the value for the original enzyme preparation. An 8.4-fold purification had been achieved.

b. Purification of Mercaptalbumin

Bovine serum albumin is a mixture of mercaptalbumin, containing one thiol group/mole, and non-mercaptalbumin in which the thiol group is masked by cysteine or gluthathione. Commercial fractions of albumin are 60-70% with respect to mercaptalbumin.

Bovine serum albumin from Sigma Chem. Comp., USA, was defatted through treatment with carbonblack. Monomeric serum albumin was prepared through gel filtration on Sephadex G-200 (reg. trademark); 380 mg of the monomeric alubumin, having a thiol content of 0.6 thiol groups/mole, was dissolved in 80 ml of 0.1 M Tris-HCl buffer, pH 7.5, which was 0.3 M with respect to KCl and 1 mM with respect to EDTA. This solution was applied to a 3.2 × 18 cm column, packed with 2-pyridinedisulphide gel, at a rate of 11 ml/h. The elution was continued until $A_{278} < 0.03$. Covalently bonded material was released through the introduction of 25 mM cysteine dissolved in the elution buffer. After gel filtration on Sephadex G-25 (reg. trademark) in 0.1 M sodium acetate buffer of pH 5.4, made 0.3 M with respect to KCl and 1 mM with respect to EDTA, this material was shown to contain 1.00–1.02 thiol groups/mole.

XII. PREPARATION OF THIOSULPHATE GELS AND THIOL GELS BASED ON EPICHLOROHYDRIN CROSS-LINKED DEXTRAN 5 g of epichlorhydrin cross-linked dextran (Sephadex G-150, reg. trademark, from Pharmacia Fine Chemicals, Uppsala) was suspended in 200 ml 0.5 M sodium hydroxide. To the suspension was added 250 mg $NaBH_4$ and 15 ml epichlorohydrin. The mixture was stirred and the temperature of the reaction vessel was gradually raised from 23° to 60° C over a period of 30 minutes. The reaction was allowed to continue at 60° C for 2 hours. The product was subsequently washed on a Büchner funnel, first with water and then with 0.5 M sodium phosphate buffer of pH 7. The gel product was then suspended in 100 ml of a 2 M sodium thiosulphate solution and allowed to react for 20 hours at room temperature under slow shaking of the reaction vessel. The resulting "Bunte Salz" gel was washed with water and in a 0.2 M $NaHCO_3$ solution, 1 mM with respect to EDTA. The gel was then reduced with 300 mg dithiothreitol dissolved in 20 ml of the 0.2 M $NaHCO_3$/1 mM EDTA.

Thiol analysis showed 230 $\mu$moles SH/g dry product.

40% of the thiol groups could be activated through treatment with 2,2'-pyridine disulphide.

Coupling of mercaptalbumin at pH 8.0 yielded an albumin-Sephadex conjugate containing 2.6 $\mu$moles albumin/g dry product.

The "Bunte Salz" gel could be directly activated through treatment with 2,2'-pyridine disulphide or tetramethylthiuram disulphide. These products could be used to conjugate mercaptalbumin yielding respectively 1.1 and 2.4 $\mu$moles albumin/g dry product.

XIII. PREPARATION OF THIOSULPHATE GELS AND THIOL GELS BASED ON EPICHLOROHYDRIN CROSS-LINKED POLYVINYL ALCOHOL 30 ml of epichlorohydrin cross-linked, beaded polyvinyl alcohol gel was suspended in 24 ml of 1 M sodium hydroxide; 4.5 ml of epichlorohydrin was added to the suspension. The reaction conditions were otherwise as described for preparation of the corresponding dextran derivative.

The gel was then treated with 30 ml of a 2 M sodium thiosulphate solution for a period of 20 hours.

Reduction of the product was performed with 500 mg of dithiothreitol dissolved in 10 ml 1 M $NaHCO_3$/1 mM EDTA.

Thiol analysis indicated 300 $\mu$moles SH/g dry product. The gel reacted with anisaldehyde at pH <1 forming a mercaptal. The thio-aldehyde could be released from the gel by an aqueous solution of $HgCl_2$.

XIV. PRODUCTS BASED ON CELLULOSE a. Preparation of "Bunte Salz" cellulose and Thiol Cellulose 5 g of powdered cellulose was mercerized in 5 M sodium hydroxide for a period of 24 hours at 0° C in a nitrogen atmosphere. The product was washed with 0.5 M sodium hydroxide on a glass filter and subsequently suspended in 25 ml 0.5 M sodium hydroxide. To the suspension were added 250 mg of $NaBH_4$ and 5 ml of epichlorohydrin. The reaction mixture was stirred and the temperature of the mixture was gradually (30 minutes) raised to 60° C, where it was kept for the remainder of the reaction (2 hours). The resulting product was washed on a filter, first with water and then with 0.5 M sodium phosphate buffer of pH 7.0. The product was subsequently suspended in 25 ml of a 2 M $Na_2S_2O_3$ solution, with which it was allowed to react for 20 minutes at room temperature under stirring. After this step the polymer was washed with water followed by 0.2 M $NaHCO_3$/1 mM EDTA. Reduction was carried out through treatment with 200 mg dithiothreitol dissolved in 10 ml 0.2 M $NaHCO_3$/1 mM EDTA. Analysis of thiol content indicated 460 $\mu$moles SH/g dry product. Thiol-cellulose derivatives did absorb copper or mercury ions out of highly diluted solutions of cupric sulphate or mercuric nitrate. The metal ions could be desorbed by disodium-EDTA.

b. Preparation of Cellulose Containing Vicinal SH-groups 5 g of powdered cellulose was mercerized according to the description above. The mercerized product was suspended in 10 ml of 5 M sodium hydroxide and 250 mg $NaBH_4$ was added to the suspension together with 1 g of alyl bromide. The mixture was kept at 70° C for 6 hours under stirring and reflux condensation. The resulting product was washed with mixtures of ethanol and water with 96% ethanol as the final washing medium. The cellulose product was then suspended in 10 ml of carbon tetrachloride to which suspension bromine was added until a non-vanishing color was obtained. The adduct was then washed with ethanol and water.

From $Na_2S.9H_2O$ (Merck, Darmstadt) was made an aqueous solution of 1 M "sodium sulphide". The brominated ellulose ether was incubated with 5 ml of the "sodium sulphide" solution for 6 hours at room temperature. The resulting product was first washed with water, then with 1 mM HCl and finally again with water. The product showed a thiol content of 410 $\mu$moles SH/g dry product. The cellulose derivative did absorb copper or mercury ions from very dilute solutions of cupric sulphate or mercuric nitrate. Around 40% of adsorbed metal ions could be desorbed by disodium EDTA. The remainder has to be viewed as bound by vicinal SH-structures.

XV.

a. Preparation of 2-Pyridine Disulphide Agarose 20 g of washed and suction dried agarose gel (2% carbohydrate content) was suspended in 16.5 ml 1 M sodium hydroxide solution. Water was added to give a total volume of 50 ml. To the suspension was added 3.1 ml epichlorohydrin and the mixture was allowed to react for 20 minutes at room temperature and subsequently for 2 hours at 60° C. The gel was washed on a glass filter, first with water, than with a 0.5 M phosphate buffer of pH 6.3. It was subsequently left to react for 6 hours at room temperature with 20 ml of a 2 M sodium thiosulphate solution. The resulting product was washed on a glass filter with a 1 M sodium chloride solution followed by water. A subsequent sulphur analysis showed 1760 $\mu$moles S/g dry product.

The product was suspended in 50 ml of a solution consisting of 50% methanol and 50% 0.1 M sodium bicarbonate solution, which was made 1 mM with respect to EDTA. Upon the addition of 1.2 g of pyridine disulphide to the suspension, the mixture was left to react for 48 hours at 60° C. After careful washing with methanol and water the product was subjected to nitrogen analysis, which showed 526 μmoles N/g dry product.

b. Coupling of Gluthathione

A column was packed with 3.4 ml of the 2-pyridine disulphide agarose described in example XV(a).

A 5 mM solution of gluthathione in a 0.1 M sodium acetate 0.1 mM EDTA buffer of pH 4.0 was pumped through this column at a rate of 5 ml/h. A total of 43 ml of the gluthathione solution was used and the product was washed first with a 0.1 M sodium acetate buffer (pH 4.1) which was made 0.1 M with respect to sodium chloride, then with a 0.1 M sodium bicarbonate solution. The product was found to contain 415 μmoles of glutathione per g dry product.

c. Coupling of Coenzyme A 2-pyridine disulphide agarose (0.9 g) was washed with 0.1 M sodium acetate buffer of pH 4.0 and suction dried. The gel was then suspended in 5 ml of the acetate buffer, which was now made 0.1 mM with respect to EDTA; 27 mg of CoA was added to the suspension. The mixture was left to react for 4 hours at 23° C and the resulting product was then washed with a 0.1 M sodium acetate buffer which was 1 M with respect to sodium chloride for 5 hours. It was subsequently washed with water for 2 hours, then with a 0.1 M sodium bicarbonate-1 M sodium chloride solution for 24 hours, and finally with water for 2 hours.

The uptake of CoA amounted to 220 μmoles/g dry product. The coupled coenzyme can be completely desorbed by dithiothreitol.

d. Coupling of Urease

Urease (Sigma, tkype IV) was adsorbed by 2-pyridine disulphide agarose until saturation. The suspension medium was 0.1 M Tris-HCl buffer of pH 7.2.

The product was extensively washed, whereupon it was shown to contain 360 mg protein/g dry conjugate. The enzyme could be desorbed by a 50 mM dithiothreitol solution. After gel filtration the urease preparation showed a specific activity 6.2 times that of the starting material.

XVI.

a. PREPARATION OF DISULPHIDE-AGAROSE GEL THROUGH TREATMENT OF ALLYLTHIOSULPHATE ESTER GEL WITH TETRAMETHYLTHIURAME-DISULPHIDE

The preparation is carried out in analogy with the preparation of 2-pyridine disulphide gel described under XV(a).

b. Coupling of Gluthathione

The coupling reaction was carried out in analogy with coupling to 2-pyridine disulphide gel. Analysis of the glutathione content showed 230 μmoles of gluthathione/g dry product. After reduction with 50 mM dithiothreitol solution a similar analysis indicated complete removal of gluthathione groups.

XVII. ACTIVATION OF THIOL AGAROSE BY MEANS OF DIETHYLAZODICARBOXYLATE

In the following series of experiments use was made of a thiol agarose gel obtained from beads containing 6% agaraose according to procedures I(a), IV(a) and V(a). The product was characterized by a thiol content of 730 μmoles SH-groups/g dry product.

a. Activation 5 g of suction dried thiol gel was suspended in 5 ml of 96% ethanol, whereupon 0.5 ml diethylazodicarboxylate was added to the suspension. The stirred mixture was allowed to react for 1.5 hours at 22° C, after which it was washed with 50% ethanol, with 1 M sodium chloride solution and with water. After drying at 100° C under vacuum for 15 hours, the product was shown to contain 1.6% nitrogen.

b. Coupling of Gluthathione 1 g of activated gel from the preparation described above was suspended in 1 ml of 1 M acetate buffer at pH 4.5; 20 mg of gluthathione was added and allowed to react for 4 hours at 22° C under stirring. The product was washed first with a 0.1 M acetate buffer which was 1 M with respect to sodium chloride, second with a 0.1 M bicarbonate solution, 1 M in sodium chloride, third with water, and fourth with acetone. Aminoacid analysis showed a gluthathione content of 610 μmoles/g dry product.

In an analogous experiment the coupling reaction was carried out at pH 7.0, which resulted in a product containing 65 μmoles of glutathione/g dry product.

The activated gel was stored at +4° C as an aqueous suspension. After one month its capacity for coupling had been reduced by 6%.

c. Adsorption and Desorption of Urease

The experiment was carried out in analogy with the description under XI (a) but with the adsorption taking place at pH 6.9. After desorption with dithiothreitol and subsequent gel filtration the specific activity was determined for the urease protein. It was found that a 5.2-fold purification had been achieved.

XVIII ACTIVATION OF THIOL AGAROSE BY MEANS OF DIISOPROPYLAZODICARBOXYLATE OR METHYLPHENYLAZOFORMATE AND THE SUBSEQUENT COUPLING OF GLUTATHIONE a. Diisopropyl Azodicarboxylate

The activation was carried out in analogy with the description under XVII (a). The product showed a nitrogen content of 1.3%.

Coupling of glutathione was carried out at pH 4.5 in analogy with XVII (b) and the resulting product showed a glutathione content of 395 μmoles/g dry product.

b. Methylpehnylazoformate

The activation proceeded in analogy with the above example yielding a product which contained 0.5% nitrogen.

The coupling of glutathione was likewise performed as in the previous example resulting in a product with a glutathione content of 11 μmoles/g dry product.

XIX. CHEMICAL MODIFICATION OF DISULPHIDE-IMMOBILIZED PROTEIN (I) THROUGH THE ATTACHMENT OF PROTEIN (II) AND SUBSEQUENT REDUCTIVE RELEASE OF THE PROTEIN (I) - PROTEIN (II) COMPLEX

The above set of experiments have been carried out using papain as "protein (I)" and chymotrypsin as "protein (II)".

20 mg of papain (0.5 SH-group/mole), dissolved in 5 ml 0.1 Tris-HCl buffer at pH 8.2, was mixed with 5 g of washed (in the same tris-buffer) and suction dried pyridyldisulphide-activated mercaptohydroxypropylether-Sepharose gel. The reaction was allowed to take place at room temperature for 5 hours under gentle stirring. The resulting papain-Sepharose conjugate was then washed on a glass filter with the following solutions:

1. 0.1 M Tris-HCl buffer, 1 M NaCl, 1 mM EDTA pH 8.2 (200 ml)
2. 0.1 M Na-acetate buffer, 1 M NaCl, 1 mM EDTA pH 4.5 (200 ml)
3. 0.1 M Na-phosphate buffer pH 6.5

Excess liquid was then sucked off the gel, which was subsequently suspended in 15 ml 0.1 M Na-phosphate buffer of pH 6.5; 15 mg of α-chymotrypsin, 100 μl cyclohexylisonitrile and 100 μl acetaldehyde were then added and the reaction mixture was kept under rotation for 2 hours at 23° C. The gel enzyme conjugate was packed into a column and washed with the following solutions at a flow rate of 10 ml/h:

| 1. | 0.1 M Na-phosphate buffer pH 6.5 | 2 hours |
| 2. | 0.1 M Na-acetate buffer, 1 M NaCl pH 4 | 6 hours |
| 3. | H$_2$O | 3 hours |
| 4. | 0.1 M NaHCO$_3$-1/M NaCl | 3 hours |
| 5. | 0.1 M NaHCO$_3$-1/mM EDTA | 3 hours |

The papain-α-chymotrypsin conjugate was then released from the gel through reduction with a 20 mM cysteine solution in 0.1 M NaHCO$_3$-1/mM EDTA which was pumped through the column. Fractions showing UV absorbance at 280 nm were pooled and exposed to gel filtration on Sephadex G-75. (This step was introduced to eliminate the excess reducing agent and released 2-thiopyridone etc.). The fraction corresponding to the papain-60 -chymotrypsin conjugate (based on molecular weight considerations) also exhibits chymotryptic activity (measured as hydrolysis of N-acetyl-L-tyrosine-ethyl ester) and papain activity (hydrolysis of N-benzyl-arginine-ethyl ester).

What we claim is:

1. A product designed for separation purposes, for ion exchange purposes or as basic material for the preparation of various derivatives designed for separation purposes, for the purpose of adsorbing or immobilizing various compounds of in particular biochemical interest, as well as products consisting of derivatives of such product, characterized in that they consist of a water-insoluble hydroxyl or amino group containing polymer substituted with organic side-chains each containing one or more thiosulphate groups (—S$_2$O$_3$- groups) or derivatives of such groups.

2. A product as claimed in claim 1, characterized in that the polymer is a gel.

3. A product as claimed in claim 1, characterized in that the polymer is agar or an agar derivative.

4. A product as claimed in claim 1, characterized in that the substituting organic side chains have the general formula where R is CH$_2$, CH$_2$—CH$_2$—SO$_2$ or CH$_2$—CH(OH)—CH$_2$—O—R$_2$—O—CH$_2$ R$_2$ being a straight chain or branched alkylene group, Z is H and/or alkyl, R' is H, alkyl, alkenyl or aryl and X is OH, H or S$_2$O$_3$- when Y is S$_2$O$_3$- or X is S$_2$O$_3$- when Y is OH, H or S$_2$O$_3$.

5. A product as claimed in claim 1, characterized by the general formula 6. A product as claimed in claim 1, characterized by the general formula 7. A product as claimed in claim 1, characterized by the general formula 8. A product as claimed in claim 1, characterized by the general formula 9. A product as claimed in claim 1, characterized in that said S$_2$O$_3$- groups, either all of them or a fraction thereof, have been converted into or replaced by —SH groups.

10. A product as claimed in claim 9, characterized in that the —SH groups, all of them or a fraction thereof, have been converted into —S—S— (disulphide) groups.

11. A product as claimed in claim 8, characterized in that the thiosulphate groups, either all of them or a fraction thereof, have been converted into or replaced by —SH groups.

12. A method for the preparation of products as claimed in claim 1 wherein the polymer is first activated by a reagent containing at least two bi-functional groups in a manner such that at least one of the reactive functional groups in each molecule is bonded to the polymer leaving a sizeable number of the remaining groups in an unreacted but reactive form whereupon, after elimination of excess reagent, the thereby activated polymer is led to react with a thiosulphate solution.

13. A method for the preparation of a product as claimed in claim 5, wherein the activation reagent consists of an epihalohydrin in alkaline solution or of a substance which in alkaline solution gives rise to dibromopropanol.

14. A method for the preparation of a product as claimed in claim 6, wherein the activating reagent consists of a bis-epoxide in alkaline solution or of a substance which in alkaline solution gives rise to a bis-expoxide.

15. A method for the preparation of a product as claimed in claim 7, wherein the activating reagent consists of divinylsulphone, or a derivative thereof, in alkaline solution.

16. A method for the preparation of a product as claimed in claim 8, wherein the polymer is first reacted with allyl bromide followed by the addition of bromine to the produced allyl polymer, whereupon the resulting product is reacted with a thiosulphate in solution.

17. A method for the transformation of products as claimed in claim 9 into thiol-polymers, wherein the conversion product from a thiosulphate-polymer is reacted with a solution of a compound which has the capacity to transform the $-S_2O_3$ groups into $-SH$ groups.

18. A method as claimed in claim 17, wherein the transformation of thiosulphate into thiol occurs through reaction with a solution of 1,4-dimercaptobutane or derivatives thereof.

19. A method as claimed in claim 18, wherein the reducing agent is a solution of threo- or erythro-1,4-dimercapto-2,3-butanediol.

20. A method for the preparation of thiol compounds wherein the water-insoluble polymer, activated as in claim 13, is directly treated with a solution of sodium sulphhydrate.

21. A method for the preparation of products as claimed in claim 10, wherein thiol polymers are exposed to an oxidizing reagent.

22. A method for the preparation of thiol compounds wherein the water-insoluble polymer, activated as in claim 14, is directly treated with a solution of sodium sulphhydrate.

23. A method for the preparation of thiol compounds wherein the water-insoluble polymer, activated as in claim 15, is directly treated with a solution of sodium sulphhydrate.

24. A method for the preparation of thiol compounds wherein the water-insoluble polymer, activated as in claim 16, is directly treated with a solution of sodium sulphhydrate.

25. A method wherein thiol compounds as claimed in claim 1 are used to prepare substitution products, in which the thiosulfate polymer is transformed in thiol polymer and H in the $-SH$ group is thereafter replaced by organic radicals which can be introduced into thiols in solution and the thiol polymers undergo relations which involve the $-SH$ groups of the polymer without alteration of the physical structure of said polymer.

26. A product as claimed in claim 1, characterized in that the polymer is polyvinyl alcohol.

27. A product as claimed in claim 1, characterized in that the polymer is cellulose.

28. A product as claimed in claim 1, characterized in that the polymer is a cross-linked polysaccharide.

29. A product as claimed in claim 1, characterized in that the polymer is an amino-substituted polyacryl amide.

* * * * *